United States Patent [19]
White, Jr.

[11] Patent Number: 5,136,825
[45] Date of Patent: Aug. 11, 1992

[54] APPARATUS AND METHOD FOR COMPACTING FLEXIBLE, COMPACTIBLE ARTICLES

[75] Inventor: Edwin C. White, Jr., Siler City, N.C.

[73] Assignee: Family Health International, Durham, N.C.

[21] Appl. No.: 750,928

[22] Filed: Aug. 28, 1991

[51] Int. Cl.⁵ .................. B65B 63/04; B65B 67/04
[52] U.S. Cl. .................... 53/429; 53/117; 53/390; 53/436; 53/529
[58] Field of Search ............... 53/429, 430, 116, 117, 53/390, 436, 529, 523

[56] References Cited

U.S. PATENT DOCUMENTS

| | | | |
|---|---|---|---|
| 2,006,212 | 6/1935 | Grabler | 206/1 |
| 2,008,875 | 7/1935 | Peterson et al. | 206/46 |
| 2,321,254 | 6/1943 | Schmid | 206/63.2 |
| 2,332,857 | 10/1943 | Karg | 206/56 |
| 2,365,556 | 12/1944 | Karg | 206/63.2 |
| 2,390,900 | 12/1945 | Schmidt | 206/63.2 |
| 2,728,505 | 12/1955 | Kurkjian | 226/2 |
| 3,136,417 | 6/1964 | Clinch | 206/63.2 |
| 3,149,017 | 9/1964 | Ehrrich et al. | 161/36 |
| 3,286,435 | 11/1966 | Weinberger | 53/117 |
| 3,391,839 | 7/1968 | Gwinn et al. | 53/117 X |
| 3,588,997 | 6/1971 | Field | 29/450 |
| 3,868,809 | 3/1975 | Bledsoe | 53/117 |
| 3,992,766 | 11/1976 | Field | 29/235 |
| 4,241,828 | 12/1980 | Bourdelle et al. | 206/306 |
| 4,446,616 | 5/1984 | Waterman | 53/390 X |
| 4,576,156 | 3/1986 | Dyck et al. | 128/132 R |
| 4,738,357 | 4/1988 | Martin et al. | 206/69 |
| 4,808,174 | 2/1989 | Sorkin | 128/644 |
| 4,817,759 | 4/1989 | Taller et al. | 128/844 |
| 4,855,169 | 8/1989 | Glothlin et al. | 428/35.2 |
| 4,881,553 | 11/1989 | Grossman | 128/844 |
| 4,964,416 | 10/1990 | Foldesy et al. | 128/842 |
| 4,972,650 | 11/1990 | Egea et al. | 53/117 X |
| 5,048,263 | 9/1991 | Lau | 53/117 X |
| 5,083,414 | 1/1992 | Wu | 53/116 X |

Primary Examiner—James F. Coan
Attorney, Agent, or Firm—Steven J. Hultquist

[57] ABSTRACT

An apparatus for compacting flexible, compactible articles, comprising a pair of vertically upwardly extending and converging wall members, a platform arranged with the wall members for relative vertical movement therebetween, and a tongue member arranged with the wall members for relative vertical movement therebetween. The wall members have limit stop means associated therewith, so that during relative movement between the wall members and tongue member, the platform engages the limit stop means. Subsequently, relative movement takes place between the tongue member and the wall members and between the platform and the tongue member, such that at the end of such relative movements, the tongue member extends upwardly above upper ends of the wall members, following which the movements are reversed. An appertaining method of compacting a flexible, compactible article is disclosed. The apparatus and method fo the invention have utility in the compaction and packaging of articles such as condoms, finger cots, tubular bandages, and the like.

20 Claims, 6 Drawing Sheets

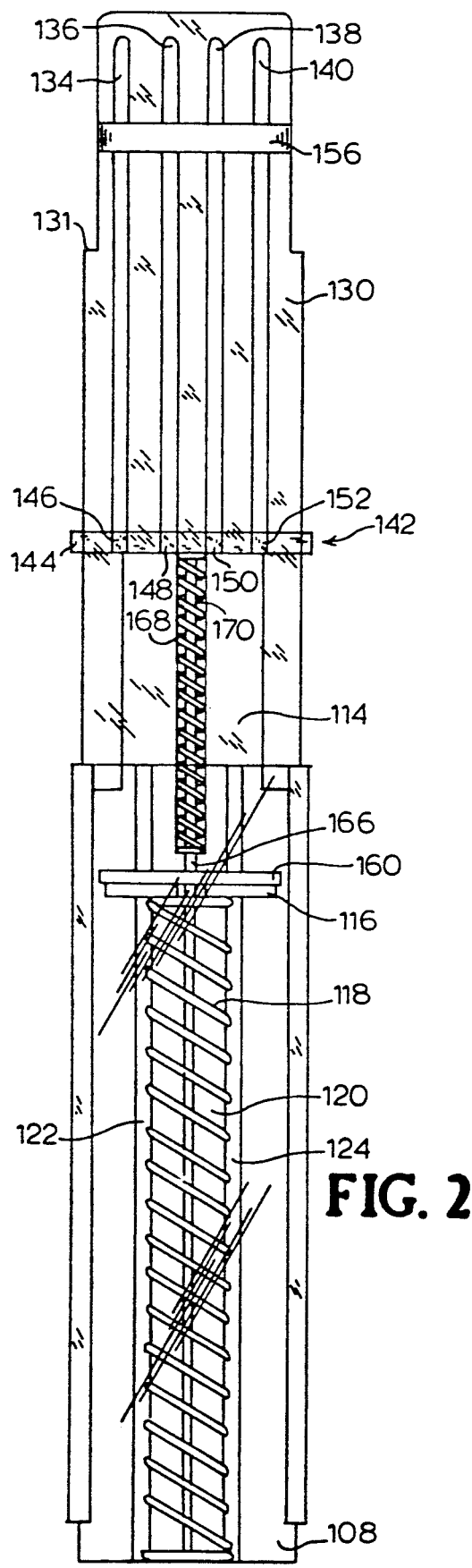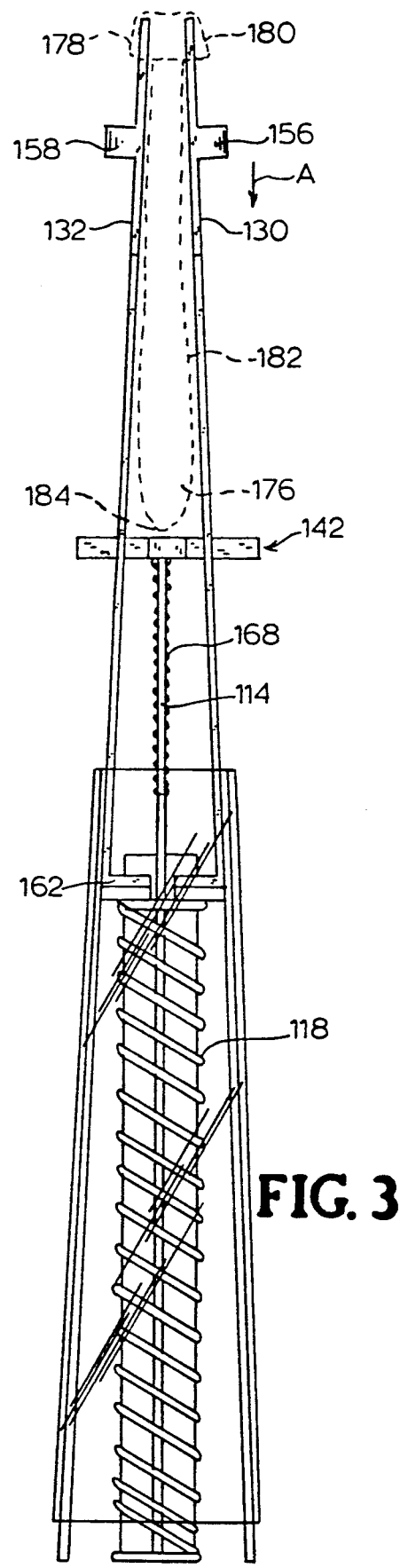

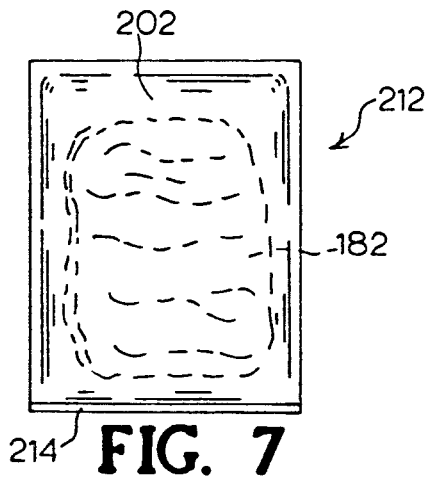
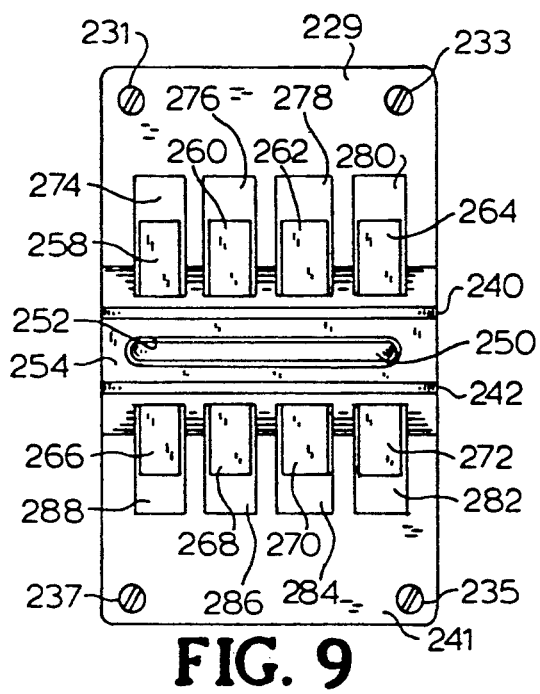
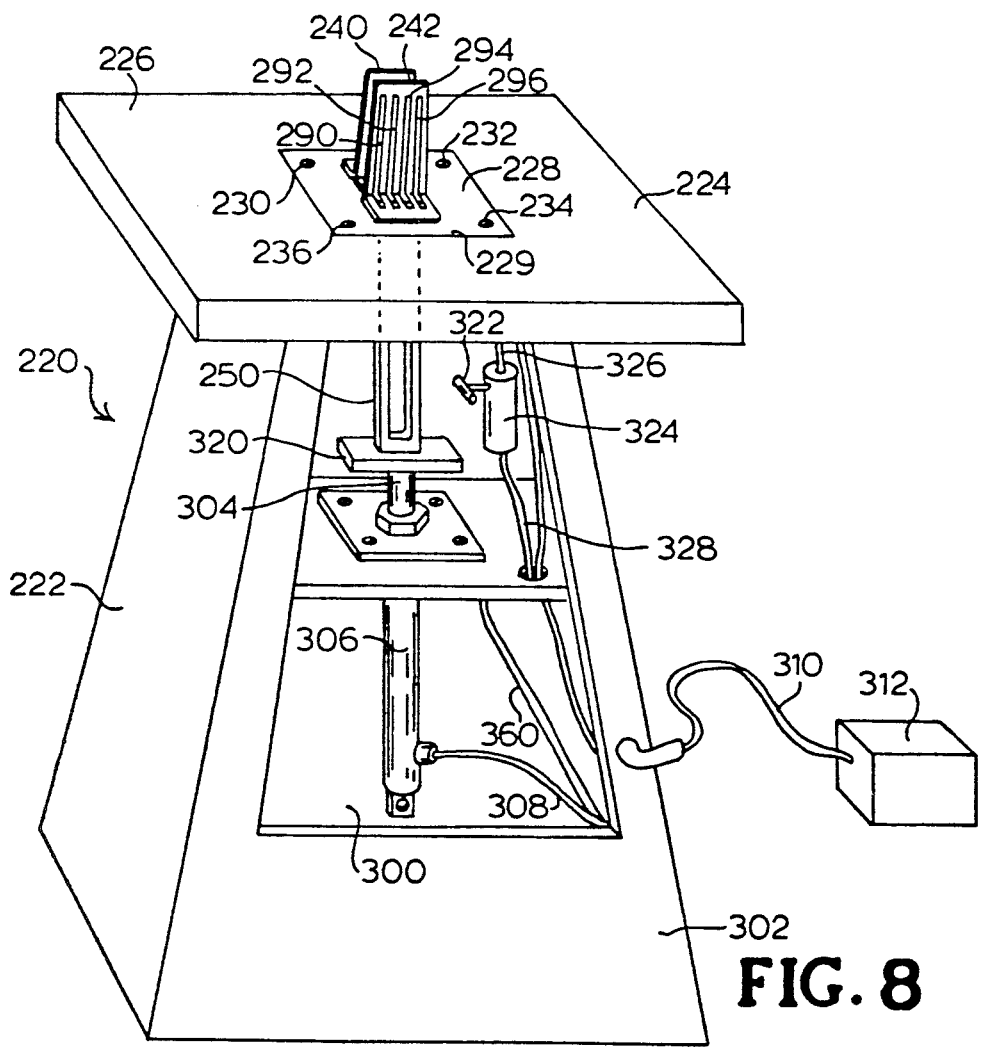

APPARATUS AND METHOD FOR COMPACTING FLEXIBLE, COMPACTIBLE ARTICLES

BACKGROUND OF THE INVENTION

1. Field of The Invention

The present invention relates to method and apparatus for compacting flexible, compactible articles such as condoms, e.g., for packaging thereof.

2. Description of The Related Art

In the manufacture of various flexible, compactible articles, e.g., condoms, finger cots, tubular bandages, and the like, it is desirable to take advantage of the flexible character of such articles in packaging same for subsequent storage and ultimate use, by subjecting the article to pre-packaging process steps such as folding, rolling, compressing, etc., so that the article has a more compact character and is more easily packaged.

By such processing, correspondingly compact packaging can be accommodated, resulting in savings in materials, transportation, and storage costs.

Various types of flexible elongate tubular articles, viz., condoms, which are subject to the above-described packaging considerations, are disclosed in U.S. Pat. No. 4,964,416 issued Oct. 23, 1990 for "CONDOM ARTICLES, AND APPARATUS AND METHOD FOR MAKING AND USING THE SAME."

FIGS. 1-11, 13-19, and 25-27 of this patent show various types of condoms featuring an annular-shaped sealing element at the proximal portion of the condom, circumscribing an interior opening of smaller size than the interior transverse cross-section of the condom (i.e., the cross-section transverse to the longitudinal axis of the condom). In addition, the condom shown in FIGS. 25-27 of this patent features flaps, or flange elements, at the proximal end opening of the device. These condoms may be formed of commodity polymeric materials, such as thermoplastic elastomers, including elastomeric polyurethanes, ethylene polymers and copolymers, polyether block amides, multiblock rubber-based copolymers, etc., as well as natural rubber, and other natural and synthetic materials.

Condoms of the foregoing type, in addition to presenting generalized packaging considerations relating to size, cost, and efficiency of packaging, present specific problems associated with the proximal sealing structure.

In addition, the condom featuring the proximal flanges poses the problem that it is desirable to package the condom such that the proximal end of the condom is "presented" when the package is opened, since the flanges serve as manually grippable parts of the condom which permit the condom to be more easily installed on the wearer's penis in the donning operation.

More specifically, the aforementioned condoms, by virtue of the proximal sealing structure defining an inner opening of smaller diameter than the diameter of the main sheath portion of the condom per se, cannot be advantageously rolled to a generally planar ring shape, as is done with conventional condoms. In conventional practice, a tubular condom article, featuring an elongated main sheath portion closed at the distal end and open at the proximal end, is longitudinally rolled on itself beginning at the proximal end. The proximal end optionally is provided with a small band or bead circumscribing the proximal opening and forming a ring. The condom is longitudinally rolled from its proximal end to its distal end, resulting in a final doughnut-shaped or toroidal roll circumscribing the distal end of the sheath.

The various condoms described in U.S. Pat. No. 4,964,416 thus cannot be advantageously rolled, due to the presence of the proximal sealing structure, which by such rolling would be undesirably stretched and deformed If the condom were to be rolled and thereupon packaged, the stretched sealing structure, as a result of sustained tensional stresses thereon, may be permanently deformed, so that the sealing capability of such structure is impaired or even fully destroyed.

These packaging difficulties are addressed in U.S. Pat. No. 4,964,416 by the constructions shown in FIGS. 22-24, which illustrate various applicator devices, with which the condom may be associated for purposes of packaging and subsequent use.

FIG. 22 of this patent, for example, shows a condom and applicator assembly, which avoids stretching of the sealing structure of the condom during its storage. The applicator is of cylindrical shape, and is formed of rigid plastic or other suitable material of construction. The condom is formed with a proximal sealing structure (retaining ring) in spaced relationship to the rear opening of the condom, so that a length of the sheath extends proximally from the sealing structure to the rear-most opening of the condom. This proximal "skirt" is stretched and folded over the applicator as shown in the patent, with the sealing structure being interiorly disposed in the cylindrical applicator and maintained in an unstretched position.

FIGS. 23 and 24 of U.S. Pat. No. 4,964,416 show a cylindrical condom applicator having on an upper end thereof a series of circumferentially spaced-apart, upwardly-extending prongs, whereby the condom may be stretched at its proximal end over diametrally opposite prongs to minimize the deformation of the condom at its proximal end, and with the condom distal to such applicator being folded or gathered in any suitable fashion, such as by the pleated folding shown in FIG. 24.

While the foregoing applicator means attempt to address the problems associated with stretching the proximal portion of the condom comprising the sealing structure, such expedients increase the cost and complexity of the condom product, and undesirably introduce an additional structural element, i.e , the applicator, which must be disposed of when the condom is used.

It would therefore be a significant advance in the art, and is an object of the present invention, to provide an improved means and method for compacting flexible, compactible articles, including articles such as condoms of the type described in U.S. Pat. No. 4,964,416, which feature a proximal sealing structure defining an interior opening of lesser diameter than the main sheath portion of the condom per se, and/or proximal flanges at the rear opening of the condom.

It is another object of the present invention to provide such compacting means and method, which compact condoms and other flexible, compactible articles in a simple and effective manner.

It is another object of the present invention to provide a compacting means of the foregoing type which may be readily operationally integrated with package-forming and delivery means, to accommodate high-speed automated manufacture and packaging of condoms and other flexible, compactible articles.

Other objects and advantages of the present invention will be more fully apparent from the ensuing disclosure and appended claims.

SUMMARY OF THE INVENTION

In a broad apparatus aspect, the present invention relates to an apparatus for compacting a flexible, compactible article, in which the apparatus comprises:

a pair of upwardly extending and upwardly converging wall members having limit stop means at an upper part thereof;

a platform arranged with the wall members for relative vertical movement therebetween, with one of:

(1) the platform, and (2) the pair of wall members, being, moveable, and the other being stationary, during such relative vertical movement;

a tongue member arranged with respect to the pair of wall members for relative vertical movement therebetween, with one of:

(1) the tongue member, and (2) the pair of wall members being stationary, and the other being vertically translatable relative thereto as a vertically motive structure; and the pair of wall members, the platform, and the tongue member being constructed and arranged such that the vertically motive structure is engageable with the platform during vertical translation thereof, and with the platform engaging the limit stop means of the wall members during translation of the vertically motive structure so as to effect subsequent relative movement between the tongue member and the wall members, and between the platform and the tongue member, such that the tongue member extends upwardly above the upper ends of the wall members at the conclusion of the relative vertical movements, and with the relative vertical movements being reversible.

In another aspect, the present invention relates to an apparatus for compacting a flexible, compactible article, such apparatus comprising:

a frame;

a pair of generally vertically upwardly extending and upwardly converging wall members, in facing relationship to one another, each such wall member having upper and lower ends and at least one vertically extending opening therein with first limit stop means at its upper extremity;

an upper platform comprising arms extending transversely outwardly through the openings of the wall members, with the upper platform having a central laterally extending slot therein;

first biasing means biasing the upper platform to an uppermost position;

a lower platform supporting the wall members at their lower ends;

second biasing means biasing the lower platform to an uppermost position;

the wall members being vertically freely slidable against the upper platform when the transversely outwardly extending arms are elevationally above the uppermost position of the upper platform;

a stationary tongue member fixedly positioned on the frame;

the lower platform being vertically slidably mounted on the frame, with the slot of the upper platform being engageable and vertically slidable along with the tongue member so that the tongue member is vertically progressively exposed with increasing vertically downward translation of the upper platform;

the first limit stop means engaging the upper platform when the wall members are vertically downwardly translated against the second biasing means and thereafter downwardly translating the upper platform with the wall members when the wall members are vertically downwardly translated against the first biasing means to progressively expose the tongue member above the upper ends of the wall members; and second limit stop means positioned on the frame for terminating the vertically downward translation of the upper platform at a selected exposure of the tongue member above the upper ends of the wall members.

The apparatus described above is particularly suitable for a relatively small-scale, manually-operated packaging operation, in which a condom is deployed with its main tubular sheath downwardly depending between the vertically extending and converging wall members, with the proximal end of the condom being draped or otherwise supported over the upper ends of the wall members, and with a suitably sized package, or packaging material, being positioned on the condom compacted on the upper portion of the exposed tongue member, when the upper and lower platforms have been downwardly translated to their lowermost (limit-stopped) positions, respectively.

Such methodology of packaging the condom results in the wall members, upper platform, and tongue member cooperatively compacting the condom as the upper and lower platforms and the wall members are downwardly translated to their respective limit-stopped positions. The condom is thereby compressed into a compacted conformation which then is medially folded over the upper end of the tongue member.

By this arrangement, a package positioned with a lower open end can be translated downwardly relative to the tongue member, to packagingly enclose the condom. The package containing the condom then may be removed from the apparatus, and its open end, through which the condom has been introduced into the package, may suitably be sealed by any conventional sealing means or method.

Alternatively, packaging components may be translated into contact with the compacted condom, e.g., on the upper end of the tongue member, with the resulting assembly of the condom and associated packaging components being further processed to provide a package enclosure containing the compacted condom. For example, the compacted condom may be "sandwiched" between two sheets of package-forming material, which subsequently is heatsealed or otherwise secured along the mated edges of the respective sheets to form the package enclosure containing the compacted condom.

In another aspect, the invention relates to an apparatus for compacting a flexible, compactible article, such apparatus comprising:

a pair of generally vertically upwardly extending and upwardly converging wall members;

a lower platform having a transverse slot therein;

a vertically extending tongue member disposed in the transverse slot, having an upper end, and vertically selectively reciprocatable between a first lower retracted position, and a second upper extended position of maximum protrusion from the transverse slot;

a second platform element reposable on the lower platform when the tongue member is in the first lower retracted position and elevatable on the tongue member to a fixed support position intermediate the first and second positions of the tongue member during rise of the tongue member from the first to the second position, such that the upper end of the tongue member continues to rise and vertically upwardly displace from the second platform element after the second platform element has reached its fixed support position, and after the tongue member has reached its second position and subsequently is vertically downwardly translated from the second position, the second platform element is lowerable thereon down to the lower platform for repositioning thereon; and means for vertically selectively reciprocating the tongue member between the first and second positions.

The vertically selectively reciprocating means described in the preceding paragraph may suitably comprise a pneumatic, hydraulic, electrical, or other automatic power system, or alternatively, a manual system, which provides for selective vertical reciprocation of the tongue member between the first and second positions.

Concurrently, a package may be manually or automatically positioned above the tongue member, such that an article downwardly suspended from upper end portions of the wall members is compacted into a folded conformation between the generally vertically upwardly extending and upwardly converging wall members as the tongue is upwardly translated. The article with further rise of the tongue member is medially folded over the upper end of the tongue member and directed into the overlying package.

As an alternative to utilizing a pre-formed package for containment of the compacted condom at the locus of the tongue member, the package may itself be formed at such locus to enclose the compacted condom. For example, the package may be formed at this location from packaging material being drawn from a reel and folded over the compacted condom on the tongue member. Alternatively, packaging material from two reels may be brought together around the compacted condom reposed on the tongue member, with the package formation being at least partially completed at such location.

As will be described more fully hereinafter, it is desirable to compact the condom, when of a type having proximal flanges, so that the flanges are on the outside of the finally compacted article, so that the condom is "presented" to the user when the package is opened, with the flanges in a readily manually graspable position. Such desired presentational conformation of the condom is accommodated by the compacting apparatus and method of the present invention.

Accordingly, the invention contemplates a corresponding method in which the flexible, compactible article, e.g., a tubular article such as a condom, is mounted with an extremity of the article positioned at the upper ends of the wall members, and with the main body portion of the article depending downwardly between the respective wall members. With the compactible article thus positioned, the tongue member is vertically upwardly translated to effect the compaction of the article, with means for reciprocating the tongue member being actuated so that after compaction, the tongue member is vertically downwardly translated to an initial position.

While the apparatus and method of the invention are described herein, for ease of reference, as involving "vertical" and "horizontal" means and orientation, it will be appreciated that such directional terminology is intended only to facilitate the description of the invention so that parts and orientations thereof are clearly and consistently referenced with respect to one another. Accordingly, it will be recognized that the apparatus and method of the invention may be carried out with other alignments and orientations. For example, the vertically orientated structures of the illustrative embodiments hereinafter described may be mounted or deployed in a "sideways" orientation, or angular orientation, relative to the specifically described vertical orientations, depending on the flexible, compactible article desired to be compacted, and the desired operation of the system in accordance with the present invention. Accordingly, it will be understood that terms such as "vertical" and "horizontal" are intended for description purposes only, and should not be limitingly construed as regards the possible orientations and alignments in the apparatus and methodology of the invention.

Other aspects and features of the invention will become more fully apparent from the ensuing disclosure and appended claims.

BRIEF DESCRIPTION OF THE DRAWINGS

FIG. 2 is a front elevation view of the flexible, compactible article compacting apparatus of FIG. 1.

FIG. 3 is a side elevation view of the flexible, compactible article compacting apparatus of FIG. 1.

FIG. 7 is a perspective view of a packaged condom article, which has been compacted and packaged using an apparatus of the type shown in FIGS. 1-6, with the package subsequently being sealed to enclose the condom article.

FIG. 8 is a perspective view of a flexible, compactible article compacting apparatus according to another embodiment of the present invention.

FIG. 9 is a top plan view of the mounting plates which are fastened to the central table portion of the FIG. 8 apparatus.

DETAILED DESCRIPTION OF THE INVENTION, AND PREFERRED EMBODIMENTS THEREOF

Figure 4:
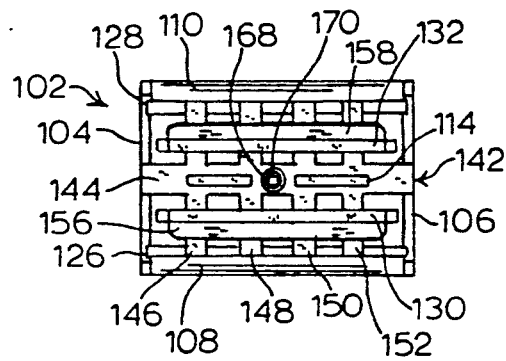
FIG. 4 is a top plan view of the flexible, compactible article compacting apparatus of FIG. 1.
Figure 1:
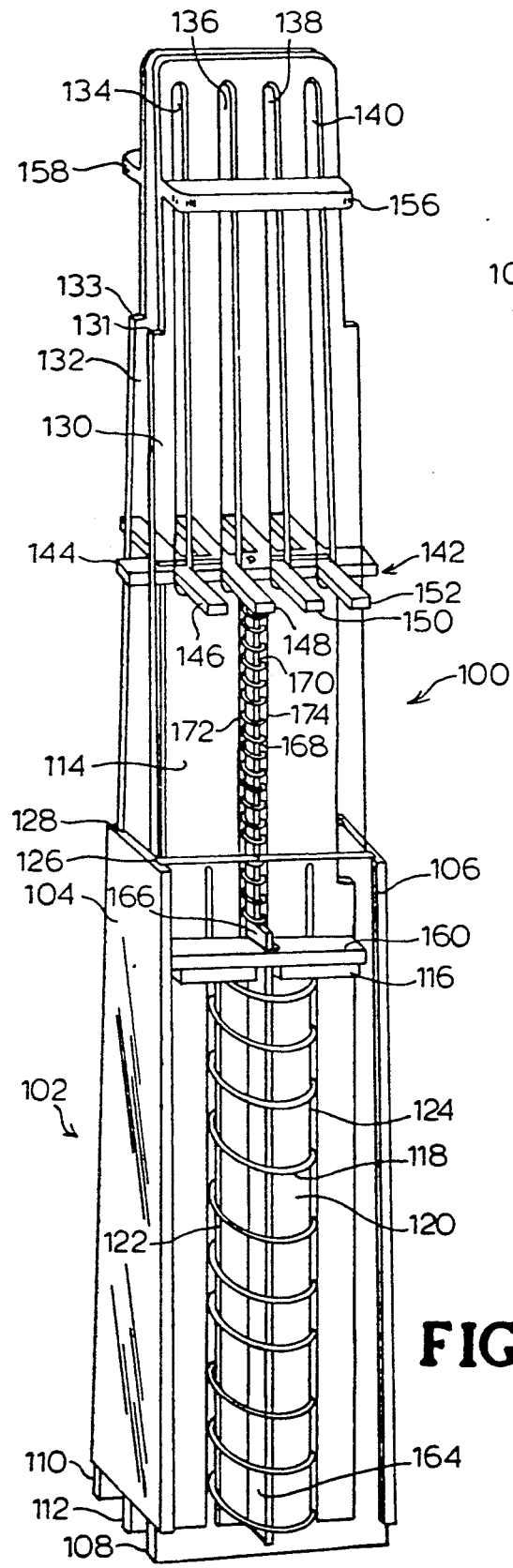
FIG. 1 is a perspective view of a flexible, compactible article compacting apparatus, according to one embodiment of the present invention.

The present invention is based on the discovery that a flexible, compactible article which is suspended between upwardly extending and upwardly converging wall members may be compacted, e.g., folded in a pleated fashion, by a platform slidably mounted on a tongue member, via relative vertical movement between the wall members and the tongue element, with corresponding relative vertical movement between the platform and the wall members until an upper stop position is reached, followed by continued relative vertical movement between the tongue member and the wall members, so that the flexible, compactible article is compacted during its confinement between the wall members and the platform, and then, as thus compacted, is medially folded at a midsection of the compacted article. In this manner, the previously compacted article is folded over the upper end of the tongue member, so that the article can be inserted, in such folded position, into the interior space of a package positioned thereabove and having an open lower end. Alternatively, the compacted article folded over the upper end of the tongue member may be contacted with packaging material and the package may be formed on the compacted article, at the tongue locus, or in any other suitable manner.

Referring now to the drawings, FIGS. 1-6 illustrate the structure and operation of a flexible, compactible article compacting apparatus according to one embodiment of the present invention.

Referring now to FIGS. 1-6, there is shown a compacting apparatus 100, comprising a frame 102 including side frame walls 104 and 106 which are vertically aligned, and joined at their front and rear edge portions to front wall 108 and rear wall 110, respectively. Intermediate the front and rear walls is medial wall 112, which at its upper end portion 114 (see FIG. 3) forms a vertically upwardly extending tongue member 114.

The flexible, compactible article compacting apparatus shown in FIGS. 1-6 is illustrated as being constructed of clear plastic or other transparent material of construction, so that interior portions of the apparatus are visible in the various views shown.

The compacting apparatus of the present invention may be formed of any suitable materials of construction, however, as consistent with the flexible, compactible article being processed, and the use and operation of the apparatus. Examples include wood, plastics, ceramics, etc. In general, the interior surfaces of the wall elements (hereinafter described) should have a low coefficient of friction with the article being compacted by the apparatus, so that the article during compaction slides easily against the confining wall members, without binding. For example, when the article being compacted is a polyurethane condom, polymeric materials such as polycarbonate may be employed, since polyurethane exhibits a suitably low coefficient of friction with the polycarbonate, so that the polyurethane condom slides easily along the confining wall surfaces during compaction when the wall members are constructed of polycarbonate.

Figure 5:
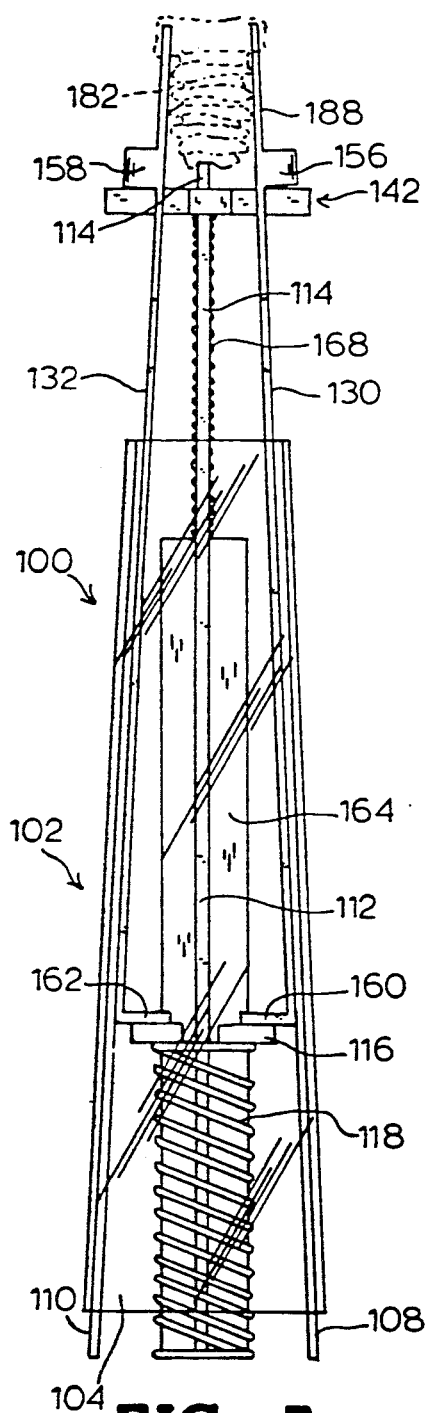
FIG. 5 is a side elevation of the compacting apparatus of FIG. 1, wherein the converging wall members feature an elongate tubular article disposed therebetween, with proximal flanges of the tubular article overlying the upper ends of the wall members, and with the article being compacted by the upper platform as it is confined between the downwardly translating wall members.

Mounted within the frame 102 is a lower platform 116 which is supported on the upper end of a biasing spring 118. The biasing spring in turn is helically wound, as shown, around a central part 120 of the medial wall 112, defined and bounded by transversely spaced-apart longitudinal slots 122 and 124 in the medial wall 112. By this arrangement, the biasing spring 118 can be axially compressed and longitudinally translated along the vertical slots 122 and 124, between a fully extended position shown in FIGS. 1-3, and a fully compressed position shown in FIG. 6, with FIG. 5 showing an intermediate compression of the spring between such fully compressed and fully extended positions.

Each of the side walls 104 and 106 of the frame 102 features slots 126 and 128 therein, in which are disposed vertically upwardly extending and converging wall members 130 and 132. The upwardly converging relationship of these wall members is shown in the side elevation view of FIG. 3, with the slots 126 and 128 correspondingly being upwardly converging from the lower end of the frame 102 to the upper end thereof. Each of these wall member features notches 131 at its respective margins, and has a series of spaced-apart, vertically extending slots 134, 136, 138 and 140 therein, forming a series of opposedly facing tracks for vertical movement of the upper platform 142 therein.

The upwardly extending and converging wall members 130 and 132 may suitably define an included angle therebetween which is on the order of about 5°, for compaction of flexible, compactible articles such as tubular condoms (see FIG. 3). In general, the included angle between the respective wall members is determined by the length of the article being compacted.

In addition, when the compacted article is packaged by means of an inverted open-mouthed package being mounted on the upper ends of the wall elements, and enclosing same (i.e., with the open mouth of the package reposing on the flanges 156 and 158 as shown in FIG. 3, so that the interior surfaces of the package are in contact with the exterior surfaces of the wall elements 130 and 132), the included angle between wall members 130 and 132 will be determined by the extent to which the invertedly positioned package is to open to receive the compacted object, and is also dependent to some extent on the thickness of the article being compacted, degree of compaction, and related factors.

The width of the upper platform 142 between the wall members 130 and 132 (see FIG. 3) defines the width of the initial folds in the article being compacted.

At their upper ends, the wall members 130 and 132 need to be in close proximity to one another to secure the article being compacted, as for example is shown in FIG. 3. The included angle between the wall elements defines an interior volume between the wall members and the upper platform 142 in which the flexible, compactible article is efficiently compacted. The specific relative orientation of the wall elements to one another, and the magnitude of the included angle therebetween, can be readily determined without undue experimentation by those skilled in the art, for a specific flexible, compactible article, and compacting apparatus.

The upper platform 142 is constructed with a laterally extending main body portion 144 to which is integrally joined a series of laterally spaced-apart, transversely outwardly extending arm elements 146, 148, 150, and 152. The laterally extending main body portion 144 of the upper platform 142 has a central laterally extending slot 152 therein, through which the upper end of tongue member 114 is engaged, in the position shown in FIG. 1.

The outwardly extending arm elements 146, 148, 150, and 152 Of the upper platform 142 serve an important function in the compacting operation which is carried out by the apparatus. They serve to prevent the flexible, compactible article from being pinched between the tongue member 114 and the inner surfaces of wall members 130 and 132.

At the upper portion of front wall 130 is provided a transversely outwardly extending flange 156. Correspondingly, a transversely outwardly extending flange 158 is secured to the upper portion of rear wall member 132, as shown. The flanges 156 and 158 provide a means for package registration, when, as previously described, an inverted open-mouth package is positioned over the upper ends of wall members 130 and 132, with the mouth opening of the package reposing on flanges 156 and 158. With such arrangement, the package is spread open during the compaction operation as wall members 130 and 132 are downwardly translated, and the finally compacted article is urged by the tongue member into the spread-open package. Flanges 156 and 158 also provide a manually grippable means which permit the respective wall members 130 and 132 to be manually downwardly translated in operation of the device.

Flanges 156 and 158 also provide the function of engaging the upper platform 142 so that the upper platform subsequent to engaging the flanges is downwardly translated with vertical downward translation of the wall members 130 and 132. Thus, subsequent to engagement of flanges 156 and 158 with upper platform 142, the lower surfaces of the flanges are maintained in contact with the top surface of the upper platform during the subsequent downward stroke.

Each of the front and rear wall members at its lower extremity is joined to a transversely inwardly extending flange. A transversely inwardly extending flange 160 is joined to the lower end of front wall member 130, and a transversely inwardly extending flange 162 is joined to rear wall member 132 (see FIG. 3). Each of these transversely inwardly extending flanges 160 and 162 are supportively reposed on the lower platform 116.

Parallel to the respective side walls 104 and 106 of the frame is a center partition 164, which is disposed at a right angle relative to the central part 120 of the medial wall 112. By this construction, the biasing spring 118 is helically coiled around the center partition 164. The center partition extends upwardly with its upper end 166 providing a support surface for a second biasing spring 168 which is helically wrapped about a central spindle 170 of the tongue member 114, with the spindle being provided between two vertically extending slots 172 and 174. The second biasing spring 168 has an upper end on which the upper platform 142 is disposed, so that the second biasing spring is axially compressible along the slots 172 and 174 between the fully extended condition shown in FIG. 1 and the fully compressed condition shown in the side elevation view of FIG. 6.

In operation, a flexible, compactible tubular article 176, shown in dotted line representation in FIG. 3, and which may be a condom of the type shown and described with reference to FIG. 27 of the aforementioned U.S. Pat. No. 4,964,416, is mounted so that it hangs downwardly between the wall members 130 and 132, with the transversely outwardly extending flanges 178 and 180 of such article being draped over the respective upper ends of the front and rear wall members as shown in FIG. 3. In this manner, the elongate main body portion 182 of the tubular article 176 is suspended, so that the distal end 184 of such article is in proximity to upper platform 142.

The transversely outwardly extending flanges 156 and 158 on the respective front and rear wall members 130 and 132 form manually grippable elements which may be downwardly pushed, against the resistances associated with the first biasing spring 118 and second biasing spring 168, so that the biasing spring 118 is initially compressed while the second biasing spring 168 remains uncompressed (see FIG. 5).

Concurrently, as the wall members 130 and 132 are downwardly translated, the upper platform 142 reposes on the upper end of the tongue member 114 without movement, while the transversely outwardly extending arm elements 146, 148, 150, and 152 of the upper platform extend through the corresponding slots 134, 136, 138 and 140 of the downwardly translated wall members. This movement of the wall members 130 and 132, relative to the stationary upper platform 142, continues until the wall members are downwardly translated to an extent at which the transversely outwardly extending flanges 156 and 158 engage the arm elements 146, 148, 150, and 152 of the upper platform 142, as shown in FIG. 5. During the downward travel of the wall members 130 and 132, the suspended tubular article confined therebetween is compacted against the stationary upper platform 142, in a generally zig-zag, pleated, folded or other compressed conformation, until the flanges 156 and 158 have contacted the arm elements of the upper platform.

Subsequently, as the downward translation of the front and rear wall members 130 and 132 is continued, the upper platform 142 is downwardly translated beneath the flanges 156 and 158 of the front and rear wall members 130 and 132, respectively. The first biasing spring 118 and second biasing spring 168 thereafter are successively further compressed, and the upper platform 142 is downwardly translated over the tongue member 114, so that the tongue member is, relative to the upper platform 142, progressively upwardly exposed until the position shown in FIG. 6 is reached.

Figure 6:
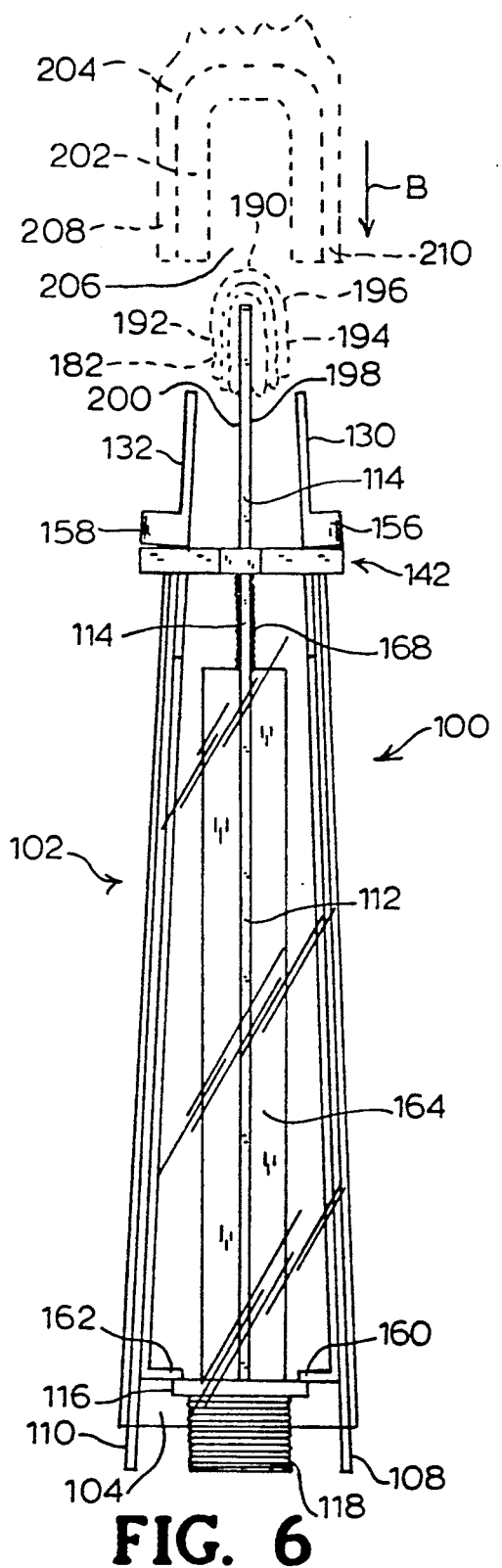
FIG. 6 is a side elevation view of the compacting apparatus of FIG. 1, shown at a further progressionary stage of operation, relative to the view shown in FIG. 5, with the folded tubular article being medially folded for packaging, and with a package deployed thereabove.
Figure 10:
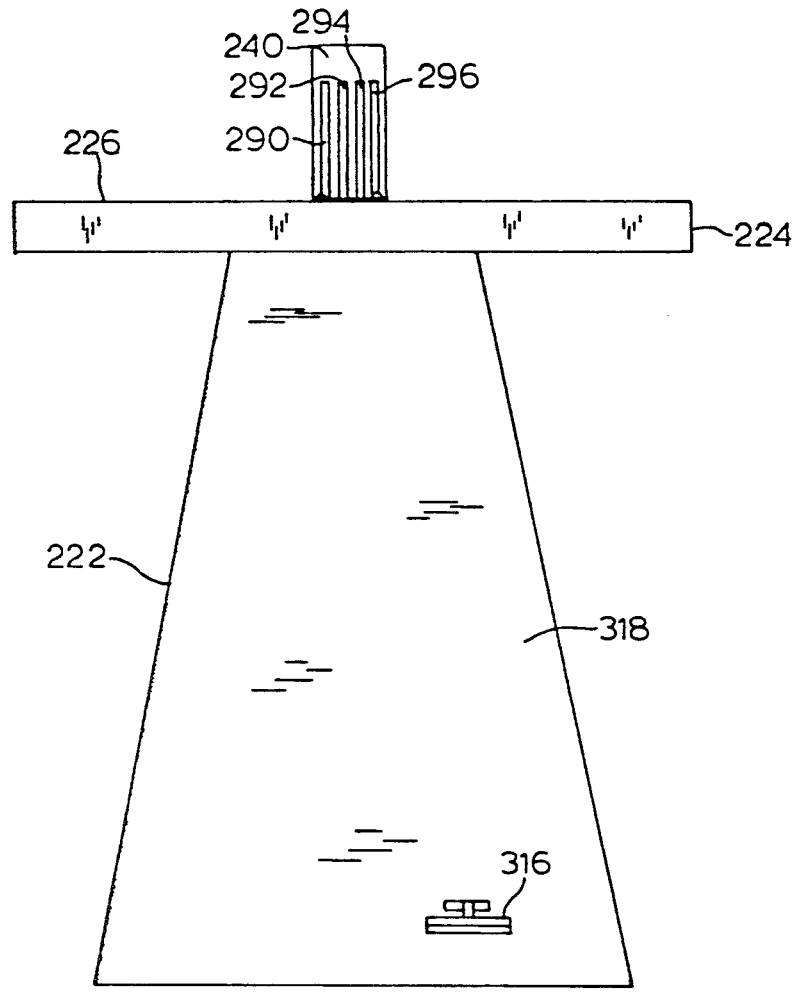
FIG. 10 is a front elevation view of the apparatus of FIG. 8.
Figure 11:
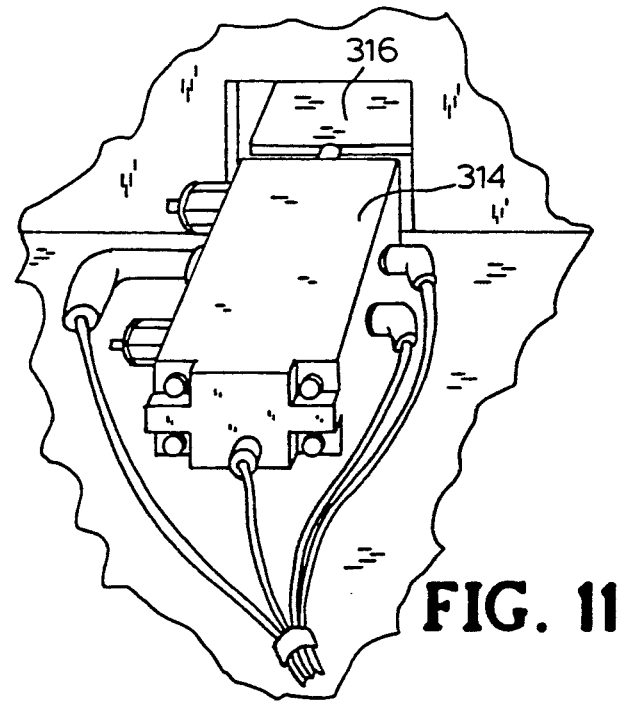
FIG. 11 is a perspective view of a portion of the hydraulic actuating means employed in the apparatus of FIGS. 8-10.

In this manner, the compacted tubular article 188 in FIG. 5 is medially folded at its midsection 190, as shown in FIG. 6, with the opposing half-sections 192 and 194 of the folded, compacted tubular article 196 being draped over the respective front and rear surfaces 198 and 200 of the tongue member 114, as shown in FIG. 6. The final folded, compacted condom article 196 thus features flanges 193 and 195 in an appropriate position for their subsequent "presentation" when the condom is taken up for application to the penis of a wearer in use.

Concurrently with the wall members 130 and 132 being in relative vertical translational movement to the tongue member 114, a condom package 202, held by a (human) hand or (mechanical) gripper means 204 is downwardly translated in the direction indicated by arrow B, so that the open end 206 of package 202 receives the compacted and folded condom article 196. Thus, the package 202 is lowered onto the compacted and folded condom article 196, following which the fingers 208 and 210 of the hand or gripper means 204 bear compressively against the package 202 containing the product condom article 196.

The thus-enfolded condom article in its package then is removed from tongue member 114 and translated to another work station (not shown) where the open end 206 of the package 202 is sealed, such as for example by heat-sealing means, to form the packaged product 212 shown in FIG. 7. The packaged product comprises package 202 having a sealed lower portion 214 (previously defining the open end 206 of the package), and containing therein the compacted and folded condom article 196.

In a packaging system utilizing the compacting and folding apparatus shown in FIG. 6, the package thus may be associated with a gripper mechanism for its application to the compacted and folded article. Alternatively, the package may simply be applied manually to the apparatus by disposing a package with its open end facing downwardly and then manually sliding the package over the upper ends of wall members 130 and 132, as previously described, so that the compacted and folded condom article is introduced into the interior space of the package, following which the package containing the condom article is manually removed from the tongue member and subjected to heat-sealing or other closure-effecting operation.

As an alternative to packaging of the compacted and folded article with a preformed package, it may be desirable in some instances to form the package about the compacted and folded article at the locus of the fully-extended tongue member. Thus, for example, it may be desirable to enfold the compacted and folded article with a sheet or ribbon of packaging material such as metal foil, Mylar ® film, or other suitable material, and to seal the resulting package at such package-forming locus. It may also be desirable to remove the compacted and folded article from the tongue member and to translate same to another location where the article is "sandwiched" between sheets of package-forming material, which then are sealed together at their edges to enclose the product article. It will recognized that the packaging of articles compacted in accordance with the present invention may be effected in any suitable manner, as necessary or appropriate for a given end use application and product article.

Although described specifically with respect to condom articles, particularly condom articles having a proximal pair of flanges associated therewith, it will be apparent that the apparatus shown in FIGS. 1-6 may be employed for the compaction of any of a wide variety of other flexible, compactible articles. Further, although the apparatus has been described in terms of compacting articles having an extremity or portion which is draped over the wall members, it will be appreciated that articles may be otherwise affixed to or mounted on the upper ends of the wall members 130 and 132, for subsequent compaction of such articles.

Accordingly, it is not necessary that the flexible, compactible article have transversely outwardly extending flanges or flaps for securement to the front and rear wall members of the apparatus, since other means may be employed to associate the flexible, compactible article with these wall members, so that the article is confined therebetween for compaction against the platform and tongue member. For example, the flexible, compactible article may be secured between the front and rear wall members by clamps, low-tack adhesives, vacuum suction, or other means or methods, to accommodate the subsequent compaction of the article.

Nonetheless, the apparatus shown in FIGS. 1-6 has demonstrated particular utility for condom articles. Such condom articles may be of generally cylindrical shape, and may feature transversely outwardly extending flanges, e.g., of the type shown and described with reference to FIG. 27 in of U.S. Pat. No. 4,964,416. Alternatively, the condom articles which may be usefully compacted for packaging in the broad practice of the invention, may comprise so-called "baggy-type" condoms which are wrapped about the penis for use.

The specific structure of the flexible, compactible article which is amenable to processing via the apparatus of the invention, may be widely varied, depending on the construction and end use of the article, and the construction of the compacting apparatus.

With respect to condom articles processible by the apparatus of the invention, such condom articles may be formed of materials such as thermoplastic elastomeric materials, as well as nonelastomeric materials such as olefinic homopolymers and copolymers, e.g., ultra-low density polyethylene. Specific materials of construction include those illustratively described in U.S. Pat. No. 4,964,416, at column 10, line 3 to column 11, line 31 thereof, and the disclosure of U.S. Pat. No. 4,964,416 hereby is incorporated herein by reference.

FIGS. 8-14 illustrate various views of a flexible, compactible article compacting apparatus according to another embodiment of the present invention.

As shown, the flexible, compactible article compacting apparatus 220 comprises a truncated pyramidal base 222, on the upper end of which is mounted a table-like lower platform 224, having a main flat top surface 226.

The central part 228 of the lower platform 224 is held in position by screw fasteners 230, 232, 234, and 236. On this central part of the lower platform are positioned mounting plates 229 and 241 whose lower portions are of generally rectangular shape (see the top plan view of FIG. 9) and whose upper portions form the wall members 240 and 242.

The mounting plates 228 and 242 are secured to the central part 228 of the lower platform 224 by means of mounting screws 230, 232, 234, and 236, at their respective outer corners, as shown.

Figure 12:
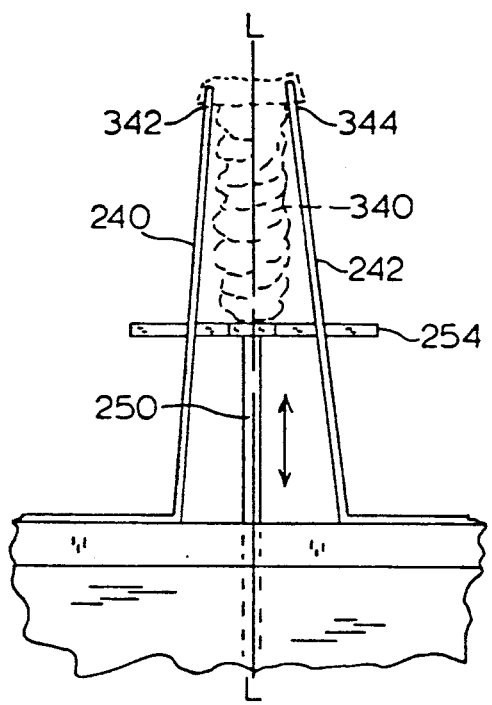
FIGS. 12 and 13 are side elevation views of a portion of the apparatus shown in FIGS. 8-10, illustrating the compaction and folding steps which are carried out in operation of the apparatus.
Figure 13:
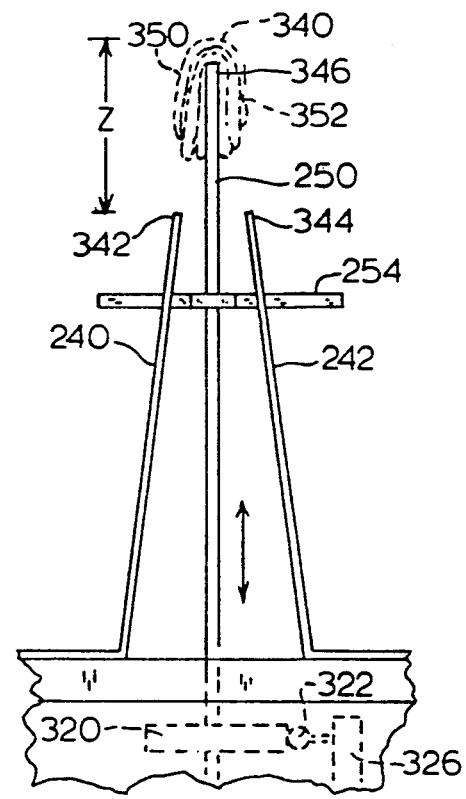

Integrally formed with the generally rectangular lower portions of the mounting plates 228 and 241, and generally vertically upwardly extending therefrom, are two transversely spaced-apart, opposedly facing wall members 240 and 242 (see FIGS. 9, 12, and 13). These opposed wall members 240 and 242 are upwardly convergent With respect to one another, each wall member being generally planar and disposed at an angle to the vertical centerline L—L of the apparatus (see FIG. 12).

Figure 14:
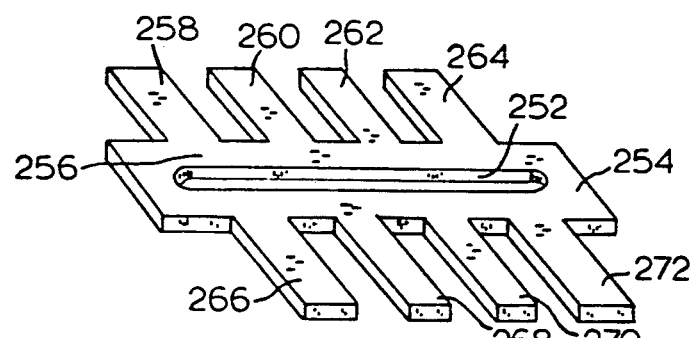
FIG. 14 is a perspective view of an upper platform element employed in the apparatus of FIGS. 8-13.

Disposed between the wall members 240 and 242, and arranged for vertically reciprocatable movement is a tongue member 250, which is reposed in a slot 252 of an upper platform element 254, shown in perspective view in FIG. 14.

As illustrated in FIG. 14, upper platform element 254 comprises a laterally extending main body portion 256 having the laterally extending slot 252 therein. Transversely outwardly extending from the main body portion 256 of this upper platform element, on either side thereof, are a series of transversely outwardly extending arms 258, 260, 262, and 264 on one side, and arms 266, 268, 270, and 272 on the other.

As show in the top plan view of FIG. 9, the mounting plates 229 and 241 are correspondingly configured with a series of slots 274, 276, 278, 280, 282, 284, 286, and 288, for matably receiving the respective arms 258-272 of the upper platform element 254.

The upwardly extending wall members 240 and 242 are formed with a corresponding series of vertically extending slots 290, 292, 294, and 296 therein (see FIGS. 8 and 10) communicating with the corresponding mounting plate slots.

By such slotted construction of the upwardly extending wall members 240 and 242, the upper platform element 254 is able to be upwardly translated on the tongue member 250 as the same is vertically upwardly translated. During such upward translation, the arms 258-272 of the upper platform element repose in and travel upwardly in the associated slots of the wall member, until the upper platform element reaches the uppermost extremity of the slots (i.e., the unslotted upper end portion of the wall members), at which point the upper platform element is restrained against further upward movement. This is shown in FIG. 13. As illustrated in such drawing, the tongue member 250 continues to be upwardly vertically translated, despite the "limit-stopped" character of the upper platform element. Thus, the tongue member becomes progressively upwardly exposed with its further translation, above the horizontal, fixedly positioned upper platform element.

Subsequently, after it has reached its maximum upper position, the tongue member 250 is lowered. The upper platform element 254 then is lowered on the downwardly translating tongue member 250 to the main top surface 226 of lower platform 224.

The upper platform element 254 may be made of any suitable material which enables the upper platform element to "secure to" (e.g., be frictionally retained by) the tongue member 250 as the tongue member is upwardly vertically translated, yet be subsequently disengaged from the tongue member when the upper platform element reaches its maximum upper (limit-stopped) position, so that the upper platform element thereafter is fixedly positioned at the upper end of the slots 290, 292, 294, and 296 in the wall members 240 and 242, without binding the tongue member as the tongue member continues to move upwardly to its own maximum vertical displacement position.

Thereafter, the upper platform element again secures to the tongue member as the tongue member moves downwardly to its initial position, so that the tip of the tongue member finally is again reposed in the slot 250 of the upper platform element, with the upper platform element in turn being reposed on the main flat top surface 226 of the lower platform 224.

The choice of material of construction for the upper platform element thus will depend on the material of construction of the tongue member, and the relative material, e.g., frictional, characteristics of the tongue member and upper platform element materials.

In some instances, it may be desirable to form the tongue member of a ferrous alloy metal, e.g., steel, and to form the upper platform element of a magnetic material, whereby the upper platform element can be magnetically retained by the tongue member during its vertical rise, with the upper platform element being disengageable from the tongue member at the upper limit-stop position of the upper platform element, as the tongue member continues its vertical upward translation, and with the upper platform element thereafter being re-engageable with the tongue as the tongue member is lowered to its initial (rest) position.

In any event, the respective materials of construction must be selected so that the tongue member is slidable against the upper platform element (1) after the upper platform element has reached its upper limit stopped position and the tongue member continues to rise, and (2) after the re-engaged upper platform element has been lowered to the lower platform and the tongue member continues to be retracted. The specific choice of materials for the tongue member and upper platform element can readily be determined by those of ordinary skill in the art, without undue experimentation.

As shown in FIG. 8, an access opening 300 is provided in the front face 302 of the base 222 of the apparatus. The tongue member 250 extends down into the interior space of the base and is joined at its lower end to a vertically reciprocatable shaft 304, which in turn is joined to a piston-containing cylinder 306. Cylinder 306 is joined by air hoses 308 and 310 to air compressor 312, which is selectively actuatable by the actuator 314 (shown in FIG. 11). The actuator in turn is manually actuated by foot pedal 316 joined to actuator and extending out of the panel 318 of the base 222 opposite panel 302.

Interposed between the lower extremity of tongue member 250 and shaft 304 is a horizontally extending contact plate 320, the right-hand side of which (as shown in FIG. 8) is positioned beneath a contact arm 322. The contact arm in turn is operatively joined to pneumatic roller switch 324. The pneumatic roller switch is joined by tubing 326 and 328 to the actuator 314 (see FIG. 11), which operates as a hydraulic controller for the system.

In operation of the system shown in FIGS. 8-14, a flexible, compactible article 340 is secured to the upper ends 342 and 344 of wall members 240 and 242, respectively. By this positioning, the article is downwardly suspended from the upper ends of the wall members. Next, the foot pedal 316 (FIG. 10) is depressed to initiate operation of the actuator 314, which then in turn directs pressurized air from air compressor 312 through air hose 308 to the hydraulic cylinder 306, which causes the piston element (not shown) thereof to vertically upwardly translate, so that shaft 304, contact block 320, and tongue member 250 in turn are all upwardly translated.

By this operation, the upper platform element 254 rises against the downwardly suspended flexible, compactible article 340, thereby compacting it, since the flexible, compactible article is transversely confined by wall members 240 and 242 (see FIG. 12). As the tongue member 250 continues to rise, the upper platform element 254 contacts the upper end surfaces of the slots 290, 292, 294, and 296, thereby restraining the upper platform element in a fixed position against further movement, as the tongue member continues to rise (see FIG. 13). The upper end 346 of tongue member 250 thus rises above the upper ends 342 and 344 of wall members 240 and 242, respectively. Concurrently, the upper end 346 of tongue member 250 medially contacts the compacted flexible article 340 to centrally fold same, so that half panels 350 and 352 of the compacted article are draped on opposite main surfaces of the tongue member, as shown in FIG. 13.

At such maximum upward translational extent of the tongue member, the compacted and folded article 340 may be inserted into a package which is suitably positioned and translated with respect thereto, or else formed-in-place as previously described, in order to enclose the compacted and folded article, and yield a packaged product article.

Thereafter, the packaged product article may be removed from the tongue member and passed to downstream sealing steps, and/or other processing for final packaging and shipment or storage.

Simultaneously with tongue member 250 achieving its maximum upward extent, the contact plate 320 contacts the contact arm 322 of the pneumatic roller switch 324. This in turn transmits a signal to actuator 314, causing it to flow pressurized air from air compressor 312 through air hose 360 to the upper end of cylinder 306, concurrently with termination of flow of pressurized air through air hose 308. In this manner, the piston in cylinder 306 is downwardly translated, to in turn effect lowering of the shaft 304, contact plate 320, and tongue member 250. As a result, tongue member 250 is lowered to a bottom, or base, position, at which the tip 346 of the tongue member is reposed in the slot 252 of upper platform element 254, and the upper platform element in turn is reposed on the main flat top surface 226 of lower platform 224.

By means of the apparatus illustrated in FIGS. 8–14, the flexible, compactible article 340 can be quickly and automatically compacted and folded, and a corresponding package can be translated into enclosing engagement with the folded article (by means such as shown and described in connection with FIGS. 1–6, which may be manual or automatic in character), or otherwise formed-in-place on the compacted and folded article. The automatic apparatus shown in FIGS. 8–14 thus may be employed in an automatic packaging operation, in conjunction with suitable package forming/delivery means, to yield a package containing the compacted and folded article.

As an illustrative embodiment of a compacting apparatus of the type shown and described with reference to FIGS. 8–14, the upper platform element 254 may suitably have a length, measured end-to-end of the main body portion 256, on the order of 2.5 inches, with a laterally extending slot 252 therein having a length of 2 inches and width on the order of ⅛ inch. Correspondingly, the upper platform element 254 may have a width (measured perpendicular to the length, from tip-to-tip of opposite arms thereof) on the order of 1.25 inches. The tongue member may be constructed so that its vertical rise above the upper ends 342 and 344 of wall members 240 and 242, respectively, is on the order of about 3 inches, corresponding to the dimension shown as Z in FIG. 13.

While the invention has been described with reference to specific details, features, and embodiments, it will be recognized that numerous variations, modifications, and other embodiments, are possible, and accordingly all such variations, modifications, and other embodiments are to be regarded as being within the spirit and scope of the present invention.

What is claimed is:

1. An apparatus for compacting a flexible, compactible article, comprising:
    a pair of upwardly extending and upwardly converging wall members having a limit stop means at an upper part thereof;
    a platform arranged with the wall members for relative vertical movement therebetween, with one of:
    (1) the platform, and
    (2) the pair of wall members,
    being moveable, and the other being stationary, during such relative vertical movement;
    a tongue member arranged with respect to the pair of wall members for relative vertical movement therebetween, with one of:
    (1) the tongue member, and
    (2) the pair of wall members,
    being stationary, and the other being vertically translatable relative thereto as a vertically motive structure; and
    the pair of wall members, the platform, and the tongue member being constructed and arranged such that the vertically motive structure is engageable with the platform during vertical movement thereof, and with the platform engaging the limit stop means of the wall members during translation of the vertically motive structure so as to effect subsequent relative movement between the tongue member and the wall members, and between the platform and the tongue member, such that the tongue member extends upwardly above upper ends of the wall members at the conclusion of the relative vertical movements, and with the relative vertical movements being reversible.

2. Apparatus according to claim 1, wherein said pair of wall members are moveable as the vertically motive structure, and said tongue member is stationary.

3. Apparatus according to claim 2, wherein the limit stop means comprise transversely outwardly extending flanges joined at their inner edges to the wall members.

4. Apparatus according to claim 1, wherein the wall members are manually vertically translatable as the vertically motive structure, and wherein the wall members are biased by biasing means to an upper position.

5. Apparatus according to claim 1, wherein the platform is vertically slidable on the tongue member, and subsequent to engagement of the limit stop means with the platform, the wall members are vertically translatable with the limit stop means in contact with the platform.

6. Apparatus for compacting a flexible, compactible article, comprising:
    a pair of vertically upwardly extending and upwardly converging wall members, in facing relationship to one another, each having upper and lower ends and at least one vertically extending opening therein, with first limit stop means at its upper extremity;
    an upper platform comprising arms extending transversely outwardly through the openings of the wall members, with the upper platform having a laterally extending slot therein;
    first biasing means biasing the upper platform to an uppermost position;
    a lower platform supporting the wall members at their lower ends;
    second biasing means biasing the lower platform to an uppermost first position;
    the wall members being vertically freely slidable against the upper platform when the transversely outwardly extending arms are elevationally above the uppermost position of the upper platform;
    a stationary tongue member fixedly positioned on the frame;
    the lower platform being vertically slidably mounted on the frame, with the slot of the upper platform being engageable with and vertically slidable along the tongue member so that the tongue member is vertically progressively exposed with increasing vertical downward translation of the upper platform;
    the first limit stop means engaging the upper platform when the wall members are vertically downwardly translated against the second biasing means and thereafter downwardly translating the upper platform with the wall members when the wall members are vertically downwardly translated against the first biasing means to progressively expose the tongue member above the upper ends of the wall members; and second limit stop means positioned on the frame for terminating the vertically downward translation of the upper platform at a selected exposure of the tongue member above the upper ends of the wall members.

7. An apparatus according to claim 6, including means for vertically downwardly translating the lower platform comprising inwardly extending flanges joined to the lower ends of the wall members and in bearing contact with the lower platform.

8. An apparatus according to claim 6, wherein the wall members at their upper portions comprise transversely outwardly extending flange elements, whereby the wall members may be vertically downwardly translated by manually gripping the outwardly extending flange elements and downwardly translating same.

9. An apparatus according to claim 6, wherein the upper platform comprises a laterally extending main body portion, to which is joined a series of laterally spaced-apart, transversely outwardly extending arms, and each of said wall members comprises a corresponding series of laterally spaced-apart, longitudinally extending slots, each having an arm of the upper platform disposed therein, and arranged such that the wall members may be vertically downwardly translated over a portion of their vertical downward travel path with the upper platform remaining in its uppermost position, and as the wall members thereafter are further downwardly translated, the upper platform is downwardly translated therewith.

10. An apparatus for compacting a flexible, compacting article, comprising:
a pair of vertically upwardly extending and upwardly converging wall members;
a lower platform having a transverse slot therein;
a vertically extending tongue member disposed in said transverse slot, having an upper end, and vertically selectively reciprocatable between a first lower retracted position and a second upper extended position of maximum protrusion from said transverse slot;
a second platform element reposable on said lower platform when said tongue member is in said first lower retracted position and elevatable on said tongue member to a fixed support position intermediate said first and second positions of said tongue member during rise of said tongue member from said first to said second position, such that the upper end of the tongue member continues to rise and vertically upwardly displace from the second platform element after the second platform element has reached its fixed support position, and after said tongue member has reached its second position and is subsequently vertically downwardly translated from the second position, the second platform element is lowerable thereon to the lower platform for repositioning thereon; and
means for vertically selectively reciprocating the tongue member between the first and second positions.

11. An apparatus according to claim 10, wherein the wall members each comprise a series of laterally spaced-apart, longitudinally extending slots therein, and the second platform element comprises a laterally extending main body portion having laterally spaced-apart, transversely outwardly extending arms joined thereto, with each said arm being disposed in a slot of each said wall member.

12. An apparatus according to claim 10, wherein the means for vertically selectively reciprocating the tongue member between the first and second positions, comprises pneumatic motive means coupled with the tongue member, and a manually actuatable switch for actuating the pneumatic motive means and initiating the reciprocation of the tongue member between the first and second positions.

13. An apparatus according to claim 10, further comprising a cabinet wherein said means for vertically selectively reciprocating the tongue member between the first and second positions is at least partially interiorly disposed, and with the cabinet comprising a top planar surface, on which the upwardly extending wall members are mounted, and wherein the top planar surface of the cabinet constitutes the lower platform.

14. A method of compacting a flexible, compactible article, comprising:
providing an apparatus including:
a pair of upwardly extending and upwardly converging wall members having a limit stop means at an upper end thereof;
a platform arranged with the wall members for relative vertical movement therebetween, with one of:
(1) the platform, and
(2) the pair of wall members,
being moveable, and the other being stationary, during such relative movement;
a tongue member arranged with respect to the pair of wall members for relative vertical movement therebetween, with one of:
(1) the tongue member, and
(2) the pair of wall members,
being stationary, and the other being vertically translatable relative thereto as a vertically motive structure; and
the pair of wall members, the platform, and the tongue member being constructed and arranged such that the vertically motive structure is engageable with the platform during vertical movement thereof, and with the platform engaging the limit stop means of the wall members during translation of the vertically motive structure so as to effect subsequent relative movement between the tongue member and the wall members, and between the platform and the tongue member, such that the tongue member extends upwardly above upper ends of the wall members at the conclusion of the relative vertical movements, and with the relative vertical movements being reversible;
securing a part of the flexible, compactible article to upper portions of the wall members such that the article is downwardly suspended from the upper portions of the wall members and hangs therebetween;
vertically translating the vertically motive structure of the apparatus to effect compaction of the article on the platform and between the opposedly facing wall members;
effecting relative movements between the tongue member and the wall members, and between the platform and the tongue member, such that the compacted article engages an upper end of the tongue member and is translated upwardly thereon between the wall members to a packaging locus comprising a maximum vertical translation of the tongue member above upper ends of the wall members; and enclosing the compacted article in a package at the packaging locus.

15. A method according to claim 14, comprising manually effecting the vertical translation of the vertically motive structure of the apparatus.

16. A method according to claim 14, comprising automatically effecting the vertical translation of the vertically motive structure of the apparatus.

17. A method according to claim 14, wherein the tongue member is stationary, and said wall members comprise the vertically motive structure of the apparatus.

18. A method according to claim 14, wherein the wall members are stationary, and the tongue member comprises the vertically motive structure of the apparatus.

19. A method according to claim 14, wherein the flexible, compactible article comprises a condom.

20. A method according to claim 14, wherein the flexible, compactible article comprises a condom having a closed distal end, a main tubular sheath portion, and a proximal end having proximal flaps associated therewith, and wherein said condom is secured to the wall members by draping of the proximal flaps over the upper ends of the wall members.

* * * * *

UNITED STATES PATENT AND TRADEMARK OFFICE
CERTIFICATE OF CORRECTION

PATENT NO. : 5,136,825
DATED : August 11, 1992
INVENTOR(S) : Edwin C. White, Jr.

It is certified that error appears in the above-indentified patent and that said Letters Patent is hereby corrected as shown below:

Column 1, line 4, insert the following:

-- GOVERNMENT LICENSE RIGHTS

The invention claimed herein was made under one or more of the following contracts: U.S. Agency for International Development Contract Nos. DPE-3041-A-00-0043 and DPE-0537-A-00-4047, and National Institutes of Heal Contract No. N01-HD-2-3143, and the U.S. Government has certain rights therein. --

Signed and Sealed this

Fifteenth Day of April, 1997

Attest:

BRUCE LEHMAN

Attesting Officer
Commissioner of Patents and Trademarks